United States Patent [19]

DiMarchi et al.

[11] Patent Number: 4,835,254

[45] Date of Patent: May 30, 1989

[54] PROCESS FOR REDUCING METHIONINE SULFOXIDE RESIDUES IN PEPTIDES OR PROTEINS

[75] Inventors: Richard D. DiMarchi; Harlan B. Long, both of Carmel, Ind.

[73] Assignee: Eli Lilly and Company, Indianapolis, Ind.

[21] Appl. No.: 88,739

[22] Filed: Aug. 24, 1987

[51] Int. Cl.$^4$ .................. C07K 15/00; C07K 17/00
[52] U.S. Cl. ................... 530/345; 530/303; 530/308; 530/313; 530/329; 530/344; 530/397; 530/399; 530/406; 530/408
[58] Field of Search ............... 530/345, 308, 313, 329, 530/399, 303, 344, 397, 406, 408

[56] References Cited

U.S. PATENT DOCUMENTS 4,745,178  5/1988  DiMarchi et al. ................. 530/345

OTHER PUBLICATIONS

Houghten, R. A., and Li, C. H. (1979) *Anal. Biochem.* 98, 36.
Savige, W. E., and Fontana, A. (1977) *Adv. in Enzymology* 47, 453.
Shechter, Y. (1986) *J. Biol. Chem.* 261, 66.
Tam, J. P., Heath, W. F., and Merrifield, R. B. (1983) *J. Am. Chem. Soc.* 105, 6442.
Fujii, N., Kuno, S., Otaka, A., Funakoshi, S., Takagi, K., and Yajami, H (1985) *Chem. Pharm. Bull., Jpn.* 33, 4587.
Yamashiro, D., (1982) *Int. J. Peptide Protein Res.* 20, 63–65.
Heath, W. F., Tam, J. P., and Merrifield, R. B., (1986) *Int. J. Peptide Protein Res.* 28, 498–507.
Yajima, H., Akaji, K., Fujii, N., Moriga, M., Aono, M., and Takagi, A., (1980) *Chem. Pharm. Bull.* 28, 2276–2278.

*Primary Examiner*—Howard E. Schain
*Attorney, Agent, or Firm*—William C. Martens; Leroy Whitaker

[57] ABSTRACT

This application discloses a process for reducing methionine sulfoxide residues in peptides and proteins to methionine residues. The process comprises subjecting said peptide or protein to a substantially anhydrous trifluoroacetic acid reaction medium containing from about 0.01M to about 3M of an organic sulfide and from about 0.01M to about 3M of a haloacid selected from the group consisting of hydrochloric acid, hydrobromic acid, and hydroiodic acid.

8 Claims, No Drawings

PROCESS FOR REDUCING METHIONINE SULFOXIDE RESIDUES IN PEPTIDES OR PROTEINS

BACKGROUND OF THE INVENTION

The sulfoxide oxidation product of methionine is a derivative which is frequently encountered in nature, as well as in synthetic peptide chemistry. The ease with which it forms makes it a common impurity in most methionine-containing peptides isolated from natural sources.

It is most advisable with purified peptides to avoid storage conditions in which sulfoxide formation is favored [Toennies, G., and Callan, T. P. (1939) *J. Biol. Chem.* 129, 481]. Once oxidized, the reduced nucleophilicity of the parent thioether renders the amino acid less susceptible to other modifications. This is the basis of its use in peptide synthesis [Iselin, B. (1961) *Helv. Chim. Acta* 44, 61] and protein modification studies [Tashjian, A., Ontjes, D., and Munson, P. L. (1964) *Biochem.* 3, 1175]. The propensity of methionine, once purified, to oxidize, in addition to the requirement of reversible protection in synthesis, has led many investigators to substitute it with alternative amino acids [Kempe, T., Chow, F., Peterson, S. M., Baker, P., Hays, W., Opperman, G., L'Italien, J. J., Long, G., and Paulson, B. (1986) *Biotechnology* 4, 565; Krstenansky, J. L., Trivedi, D., Johnson, D., and Hruby, V. (1986) *J. Am. Chem. Soc.* 108, 1696; and Schalch, D., Reisman, D., Emler, C., Humbel, R., Li, C. H., Peters, M., and Lau, E. (1984) *Endocrinology* 115, 2490].

Selective and non-destructive reduction of methionine sulfoxide-containing peptides has been a recurrent problem in peptide chemistry [Kessler, W., and Iselin, B. (1966) *Helv. Chim. Acta* 49, 1330]. Most frequently, reduction is achieved through the use of high concentrations of reducing agents such as dithiothreitol or β-mercaptoethanol at elevated temperatures [Houghten, R. A., and Li, C. H. (1979) *Anal. Biochem.* 98, 36]. The reaction rate is slow, and the process usually yields incomplete reduction. An alternative means of reduction has been dimethyl sulfide or thioanisole promotion of oxygen exchange in aqueous HCl [Savige, W. E., and Fontana, A. (1977) *Adv. in Enzymology* 47, 453; Shechter, Y. (1986) *J. Biol. Chem.* 261, 66], anhydrous HF [Tam, J. P., Heath, W. F., and Merrifield, R. B. (1983) *J. Am. Chem. Soc.* 105, 6442], 1M trifluoromethanesulfonic acid-TFA [Fujii, N., Kuno, S., Otaka, A., Funakoshi, S., Takagi, K., and Yajami, H. (1985) *Chem. Pharm. Bull., Jpn.* 33, 4587]. In these cases, reduction is facile and a variable degree of disulfide integrity can be maintained. Of notable concern, however, are the potential secondary consequences of exposure to strong acids of this nature.

Haloacids have been recognized to catalyze the transfer of oxygen from a sulfoxide to a sulfide for some time [Scorrano, G. (1973) *Acc. Chem. Res.* 6, 132]. Savige and Fontana, supra, were the first to explicitly describe the reduction of free (i.e., not part of a protein) methionine sulfoxide using 12 N HCl and dimethyl sulfide. Successful application to an oxidized lysozyme derivative was also described with minimal assessment of secondary side-reactions. They concluded that "the reaction conditions are rather severe and require HCl of high concentrations." Most recently, Shechter, supra, reported similar reduction of methionine sulfoxide in proteins through the use of dimethyl sulfide and varying concentrations of HCl. He concludes that "at 4.4–10.7 M HCl, the reaction proceeds to completion, while at lower concentrations of HCl (i.e. 1.0 M), the extent of the reduction is retarded tremendously." High performance analysis for secondary modifications was not performed in either study.

Methionine sulfoxide reduction in anhydrous HF or 1M trifluoromethanesulfonic acid-TFA is believed to occur by a different mechanism than that which occurs in aqueous HCl. In these strong anhydrous acids, reduction is believed to be a function of the acidity of the mixture and is not dependent on the nucleophilicity of the acid anion. Efficient reduction has been reported with minimal levels of undesirable modifications. However, the caustic nature of these solvents requires special handling precautions which impose severe restrictions on their use.

This invention is directed to a facile and highly selective process for treating proteins and peptides having methionine sulfoxide residues to selectively reduce such residues to methionine residues. Specifically, the process of this invention effects reduction using substantially milder conditions than those imposed by prior art methods.

SUMMARY OF THE INVENTION

Thus, this invention is directed to a process for treating peptides and proteins containing one or more methionine sulfoxide residues to reduce such residues to methionine residues, which comprises subjecting said peptide or protein to a substantially anhydrous trifluoroacetic acid reaction medium containing from about 0.01M to about 3M of an organic sulfide and from about 0.01M to about 3M of a haloacid selected from the group consisting of hydrochloric acid, hydrobromic acid, and hydroiodic acid.

DETAILED DESCRIPTION OF THE INVENTION

As indicated in the foregoing, this invention is directed to a process for selectively reducing proteins and peptides containing methionine sulfoxide residues to their corresponding methionine residue counterparts. The process will find principal utility in generating mature, biologically-active product from its oxidized precursor, the latter most often being produced as a result of the conditions employed in synthetically generating the protein or peptide. Conditions leading to oxidation of methionine residues to the sulfoxide form can appear during the course of any of a range of processing steps, including synthesis and purification of the desired protein or peptide. Without a viable method for restoring the methionine residue to its reduced state, one would be at a loss, at least in the production of large scale amounts of mature product, to obtain quantities of the desired product of any reasonable size.

The process of this invention is carried out in trifluoroacetic acid as solvent. Although not absolutely essential, it is highly preferred to conduct the process of this invention under substantially anhydrous conditions, and thus, to employ substantially anhydrous trifluoroacetic acid. It is not intended by "substantially anhydrous" trifluoroacetic acid to require affirmative measures to preclude the presence of trace amounts of water. Only the avoidance of an affirmative addition of water is intended.

To the trifluoroacetic acid is added the protein or peptide to be subjected to reduction along with an organic sulfide and a haloacid. The reagents can be added in any order. Ideally, however, the protein or peptide is first dissolved in the trifluoroacetic acid after which the organic sulfide is added followed by the haloacid.

The amount of protein or peptide added to the trifluoroacetic acid generally will be such as to provide a concentration ranging from about 0.01 to about 100 mg/ml. Preferably, the concentration will be from about 0.1 to about 20 mg/ml, and, more preferably, from about 1 to about 10 mg/ml.

The protein or peptide is reacted in trifluoroacetic acid with an organic sulfide and a haloacid. Any of a wide range of organic sulfides can be employed, the only requirement being that, apart from the reactive sulfide moiety, they be inert under the conditions of the process of this invention. Examples of typical sulfides are dimethyl sulfide, diethyl sulfide, ethyl methyl sulfide, diphenyl sulfide, dithiothrietol, cysteine, and the like. Preferred sulfides are dialkyl sulfides in which each alkyl group contains from 1 to 3 carbon atoms. Highly preferred for use in the process of this invention is dimethyl sulfide.

The organic sulfide is added to the reaction mixture to produce a concentration ranging generally from about 0.01M to about 3M. The concentration preferably is from about 0.1M to about 1M, and, more preferably, from about 0.5M to about 1M.

A remaining essential reagent is a haloacid. The haloacid is selected from hydrogen chloride, hydrogen bromide, and hydrogen iodide. The haloacid preferably is hydrogen chloride. The haloacid generally is present in the reaction mixture in an amount ranging from about 0.01M to about 3M. Preferably, the haloacid is present in an amount ranging from about 0.1M to about 1M. Within the foregoing range, it is preferred to effect the process at the lower end of the range if the protein or peptide being treated contains one or more disulfide bonds and at the upper end of the range if no disulfides are present.

Notwithstanding the foregoing discussion regarding the preference to conduct the process under anhydrous conditions, certain amounts of water normally will be incorporated in the reaction mixture by addition of the haloacid. Since the total amount of haloacid used is small and can be incorporated by addition of concentrated acid, only a small amount of water need actually be added to the mixture. The added amount is entirely tolerable in accordance with the process of this invention.

The process of this invention can be conducted over a wide temperature range, for example, generally anywhere from about 4° C. to about 45° C. Preferably, the reaction is conducted at about room temperature (about 20° C. to about 25° C.).

The reduction normally occurs quite rapidly. Although the reaction can be conducted for an extended period, e.g., about 6 hours, it can be completed in as little as 5 minutes. Customarily, therefore, the reaction is conducted for a period of from about 30 minutes to about 90 minutes.

Upon completion of the reduction, the desired product can be recovered using any of a wide range of recognized recovery techniques.

The following examples are provided to illustrate the process of this invention. They are not intended to be limiting upon the broad scope thereof.

EXAMPLE 1

Treatment of H-Phe-Met(O)-Gly-Pro-Glu-Thr-$NH_2$(FM(O)GPET $NH_2$).

The peptide FM(O)GPET-$NH_2$ (2.15 mg) was dissolved in 1.72 ml of anhydrous trifluoroacetic acid (TFA). The peptide solution was divided into seventeen 80 $\mu$l aliquots. One aliquot, serving as control, received no dimethyl sulfide (DMS) or hydrochloric acid (HCl). To the other 16 peptide solutions were added various amounts of DMS to a concentration ranging from 0.01M to 1M and concentrated HCl to an HCl concentration ranging from 0.01N to 1N. The solutions were initially mixed vigorously and then allowed to remain undisturbed at room temperature for 60 minutes. The reactions were terminated by addition of 900 $\mu$l of 0.1% aqueous TFA.

The extent of chemical modification was assessed by high performance liquid chromatography (HPLC) with an Altex Ultrasphere ODS reversed-phase column (0.46×25 cm). Chromatography was performed in 0.1% aqueous TFA at 45° C. with elution achieved through an increasing linear gradient of $CH_3CN$. Quantitation was based on peak area measurements at 214 nm. The TFA/DMS/HCl-treated FM(O)GPET-$NH_2$ yielded a peptide which displayed an identical chromatographic retention time to that of a synthetic standard FMGPET-$NH_2$. The results of the study are displayed in Table 1 following.

TABLE 1

| | REDUCTION OF FM(O)GPET-$NH_2$ | | |
|---|---|---|---|
| HCl Conc., N | DMS Conc., $M^1$ | FMGPET-$NH_2$, % Formed | FM(O)GPET-$NH_2$, % Remaining |
| 0 | 0 | 0 | 100 |
| 0 | .01 | 0 | 98 |
| 0 | 0.1 | 0 | 95 |
| 0 | 1.0 | 3 | 89 |
| .01 | 0 | 4 | 95 |
| .01 | .01 | 10 | 86 |
| .01 | 0.1 | 11 | 84 |
| .01 | 1.0 | 12 | 85 |
| 0.1 | 0 | 4 | 96 |
| 0.1 | .01 | 57 | 41 |
| 0.1 | 0.1 | 54 | 41 |
| 0.1 | 1.0 | 68 | 33 |
| 1.0 | 0 | 4 | 85 |
| 1.0 | .01 | 94 | 0 |
| 1.0 | 0.1 | 93 | 0 |
| 1.0 | 1.0 | 95 | 0 |

[1] In anhydrous trifluoroacetic acid

EXAMPLE 2

Treatment of GRF(1-45)Met(O)[27], Lys[45]-OH

GRF(1-45)Met(O)[27],Lys[45]-OH (1.68 mg) was dissolved in 1.5 ml of anhydrous trifluoroacetic acid (TFA). To 900 $\mu$l of the peptide solution were added 100 $\mu$l of dimethyl sulfide (DMS) followed by 10 $\mu$l of concentrated HCl. The solution was mixed vigorously and then was allowed to remain unstirred at room temperature. At 5, 15, 30 and 60 minutes following HCl addition, 60 $\mu$l aliquots of the reaction mixture solution were removed. Each sample was dried with $N_2$ and diluted to 1.2 ml by addition of 0.1% aqueous TFA. At the end of 60 minutes, additional concentrated HCl (7.6 $\mu$l) was added to the remaining peptide solution (760 $\mu$l), and the solution was again mixed vigorously and then allowed to remain unstirred at room temperature. At 65, 75, 90, 120 and 180 minutes after the first HCl addition, 60 μl aliquots were removed and dried over $N_2$ and diluted with 0.1% aqueous TFA as described above.

The extent of chemical modification was assessed by high performance liquid chromatography (HPLC) with a Vydac $C_4$ reversed-phase column (0.46×10 cm). Chromatography was performed in 0.1% aqueous TFA at 45° C., elution being achieved using an increasing linear gradient of $CH_3CN$. Quantitation was based on peak height measurements at 214 nm. The TFA/DMS/HCl-treated GRF(1-45)Met(O)$^{27}$, Lys$^{45}$-OH yielded a peptide which displayed an identical chromatographic retention time to that of a synthetic standard GRF(1-45)Met$^{27}$, Lys$^{45}$-OH. The results of the study are displayed in Table 2 following.

TABLE 2

Reduction of GRF(1-45)Met(O)$^{27}$, Lys$^{45}$—OH

| Time (min) | GRF(1-45)Met$^{27}$, Lys$^{45}$—OH, % Yield |
|---|---|
| 5 | 64 |
| 15 | 92 |
| 30 | 98 |
| 60 | 93 |
| 65 | 96 |
| 75 | 97 |
| 90 | 95 |
| 120 | 93 |
| 180 | 88 |

EXAMPLE 3

Treatment of Glucagon Met(O)$^{27}$

Glucagon Met(O)$^{27}$ (1.32 mg) was dissolved in 660 μl of 1M DMS in anhydrous trifluoroacetic acid (TFA). An untreated control was obtained by removing a 30 μl aliquot, drying it with $N_2$ and solubilizing it in 1.2 ml of 0.1% aqueous TFA. The peptide/TFA/DMS solution was divided into six portions. Various amounts of concentrated HCl and tryptophan were added to the solutions, and the solutions were mixed vigorously and then allowed to stand unstirred for 60 minutes at room temperature. The tryptophan was added to minimize destruction of the internal tryptophan of glucagon at position 25. Sixty μl aliquots of each solution were removed, and the reactions were terminated by rapidly drying with $N_2$ and diluting with 1.2 ml of 0.1% aqueous TFA. At the end of 60 minutes, additional concentrated HCl was added to the remaining peptide solutions. The mixtures were mixed vigorously and then allowed to remain unstirred at room temperature. Sixty minutes after the second HCl addition, 60 μl aliquots of each solution were removed and dried over $N_2$ and diluted with 1.2 ml of 0.1% aqueous TFA as described above. The extent of chemical modification was assessed by high performance liquid chromatography (HPLC) with a DuPont $C_8$ reversed-phase column (0.46×25 cm). Chromatography was performed in 0.1M, pH 7 ammonium phosphate at 45° C. with elution achieved using an increasing linear gradient of $CH_3CN$. Quantitation was based on peak area measurements at 214 nm. The TFA/DMS/HCl-treated glucagon Met(O)$^{27}$ yielded a peptide which displayed an identical chromatographic retention time to that of a synthetic standard glucagon. The results of the study are displayed in Table 3 following.

TABLE 3

Reduction of Glucagon Met(O)$^{27}$

| Trp Conc., $M^{1,2}$ | Rxn Time, min. | HCl Conc., $N$ | Glucagon, % Yield | Glucagon Met(O), % Remaining |
|---|---|---|---|---|
| 0 | 60 | .1 | 38 | 10 |
| 0 | 60 | .1 | 40 | 8 |
| 0 | 120 | .2 | 28 | 2 |
| 0 | 120 | .2 | 25 | 1 |
| 10 | 60 | .1 | 68 | 7 |
| 10 | 60 | .1 | 66 | 7 |
| 10 | 120 | .2 | 58 | 1 |
| 10 | 120 | .2 | 59 | 1 |
| 100 | 60 | .1 | 75 | 17 |
| 100 | 60 | .1 | 76 | 15 |
| 100 | 120 | .2 | 83 | 1 |
| 100 | 120 | .2 | 81 | 1 |

[1]Expressed as Molar equivalents to glucagon
[2]DMS present at 1 $M$ concentration

EXAMPLE 4

Treatment of IGF-I, Met(O)$^{59}$

IGF-I, Met(O)$^{59}$ (0.90 mg) was dissolved in 0.90 ml of anhydrous trifluoroacetic acid (TFA). The peptide solution was divided into eight 100 μl aliquots. Samples 1, 2, 7 and 8 were dried with $N_2$ prior to treatment. Each pair of samples (i.e. 1 and 2, 3 and 4, 5 and 6, 7 and 8) received identical treatment except that the even numbered samples were converted to the cysteinyl S-sulfonate prior to assay. To the samples were added various amounts of anhydrous TFA, dimethyl sulfide (DMS), and concentrated HCl. The solutions were mixed vigorously and then allowed to remain unstirred at room temperature. Some samples received additional concentrated HCl 30 minutes following the initial HCl addition. The reactions of all samples were terminated at the end of 30 or 60 minutes by dilution with 0.1% aqueous TFA or sulfitolysis of neutralized solutions.

The extent of chemical modification was assessed by high performance liquid chromatography (HPLC) with a DuPont $C_8$ Reliance reversed-phase column (0.6×4 cm). Chromatography was performed in 0.1M, pH 7 ammonium phosphate at 45° C. with elution achieved through an increasing linear gradient of $CH_3CN$. Quantitation was based on peak area measurements at 214 nm. The TFA/DMS/HCl-treated IGF-I,Met(O)$^{59}$ yielded a peptide which displayed an identical chromatographic retention time to that of a synthetic standard IGF-I. The results of the study are displayed in Table 4 following.

TABLE 4

Reduction of IGF-I Met(O)$^{59}$

| Sample No. | TFA, μl | HCl Conc., $N$ | DMS Conc., $M$ | Time, min. | Reduction, % | IGF-I, % Yield |
|---|---|---|---|---|---|---|
| 1[1] | 0 | 0 | 0 | 0 | 0 | — |
| 2[1] | 0 | 0 | 0 | 0 | 0 | — |
| 3 | 100 | .1 | 1 | 30 | 80 | 67[2] |
| 4 | 100 | .1 | 1 | 30 | 80 | 69[3] |
| 5 | 100 | .2 | 1 | 60 | 93 | 56[2] |
| 6 | 100 | .2 | 1 | 60 | 97 | 86[3] |
| 7 | 0 | 4.4 | .5 | 30 | 6.9 | <1[2] |
| 8 | 0 | 4.4 | .5 | 30 | 10 | 4.5[3] |

[1]Control
[2]Assayed as disulfide
[3]Assayed as S—sulfonate after sulfitolysis

We claim:
1. A process for treating peptides and proteins containing one or more methionine sulfoxide residues to reduce such residues to methionine residues, which comprises subjecting said peptide or protein to a substantially anhydrous trifluoroacetic acid reaction medium containing from about 0.01M to about 3M of an organic sulfide and from about 0.01M to about 3M of a haloacid selected from the group consisting of hydrochloric acid, hydrobromic acid, and hydroiodic acid.

2. Process of claim 1, in which the protein or peptide is present at a concentration ranging from about 0.01 to about 100 mg/ml.

3. Process of claim 2, in which the protein or peptide is present at a concentration ranging from about 0.1 to about 20 mg/ml.

4. Process of claim 1, in which the organic sulfide is a dialkyl sulfide in which each alkyl group contains from 1 to 3 carbon atoms.

5. Process of claim 4 in which the organic sulfide is dimethyl sulfide.

6. Process of claim 4, in which the organic sulfide is present in the reaction mixture at a concentration ranging from about 0.1M to about 1M.

7. Process of claim 1, in which the haloacid is hydrochloric acid.

8. Process of claim 7, in which the haloacid is present in the reaction mixture at a concentration ranging from about 0.1M to about 1M.

* * * * *